United States Patent
Huber et al.

(10) Patent No.: US 7,639,352 B2
(45) Date of Patent: Dec. 29, 2009

(54) DETECTION DEVICE FOR IDENTIFYING OBJECTS IN A MATERIAL STREAM

(75) Inventors: Reinhold Huber, Fürstenfeld (AT); Christian Pansinger, Graz (AT)

(73) Assignee: Binder + Co. AG, Gleisdorf (AT)

( * ) Notice: Subject to any disclaimer, the term of this patent is extended or adjusted under 35 U.S.C. 154(b) by 395 days.

(21) Appl. No.: 11/629,970

(22) PCT Filed: May 4, 2005

(86) PCT No.: PCT/AT2005/000154

§ 371 (c)(1),
(2), (4) Date: Dec. 18, 2006

(87) PCT Pub. No.: WO2006/000001

PCT Pub. Date: Jan. 5, 2006

(65) Prior Publication Data

US 2007/0182956 A1    Aug. 9, 2007

(30) Foreign Application Priority Data

Jun. 29, 2004  (AT) .............................. GM450/2004

(51) Int. Cl.
- *G01N 21/00* (2006.01)
- *G01B 11/00* (2006.01)
- *G01J 1/00* (2006.01)

(52) U.S. Cl. .................. 356/239.1; 356/399; 356/213; 356/432; 356/73

(58) Field of Classification Search ................. 356/399, 356/239.1, 73, 213, 432–435; 209/581, 588, 209/639

See application file for complete search history.

(56) References Cited

U.S. PATENT DOCUMENTS

| 3,011,634 A | 12/1961 | Hutter et al. |
| 3,097,744 A | 7/1963 | Hutter et al. |
| 3,545,610 A | 12/1970 | Kelly et al. |

(Continued)

FOREIGN PATENT DOCUMENTS

AT    395 545    6/1992

(Continued)

OTHER PUBLICATIONS

International Search Report, Nov. 2005.

*Primary Examiner*—L. G Lauchman
(74) *Attorney, Agent, or Firm*—Collard & Roe, P.C.

(57) ABSTRACT

The invention relates to a detection device for identifying objects in a material stream, preferably a cullet stream. The device comprises several light sources, which emit light in a rectilinear manner, preferably diode light sources and which are combined to form at least one optical emitter, at least one receiver that contains a lens system and a photoelectric cell, in addition to a detection section, which is located between the emitter and the receiver and is traversed by the material stream. The aim of the invention is to provide a detection device, which eliminates to a great extent the error sources that are inherent in optical lens systems. To achieve this, the light sources of an emitter are directed onto the area of intersection of the optical axis of the lens system with the lens system of the receiver that is assigned to the emitter.

10 Claims, 3 Drawing Sheets

U.S. PATENT DOCUMENTS

| | | | |
|---|---|---|---|
| 4,606,634 A | 8/1986 | Bieringer | |
| 4,699,273 A | 10/1987 | Suggi-Liverani et al. | |
| 5,894,938 A * | 4/1999 | Ichise et al. | 209/559 |
| 5,954,206 A * | 9/1999 | Mallon et al. | 209/580 |
| 6,144,004 A * | 11/2000 | Doak | 209/581 |
| 6,504,124 B1 * | 1/2003 | Doak | 209/581 |
| 2003/0035108 A1 | 2/2003 | Taniguchi et al. | |

FOREIGN PATENT DOCUMENTS

| | | |
|---|---|---|
| DE | 195 09 631 A1 | 9/1996 |
| EP | 0 375 881 A1 | 7/1990 |
| EP | 0 452 235 A | 10/1991 |
| EP | 0 479 756 | 4/1992 |
| EP | 0 479 756 A2 | 4/1992 |
| EP | 0 820 819 A1 | 1/1998 |
| GB | 1 274 449 A | 5/1972 |
| JP | 07068223 A | 3/1995 |
| WO | WO 96/03226 A | 2/1996 |

* cited by examiner

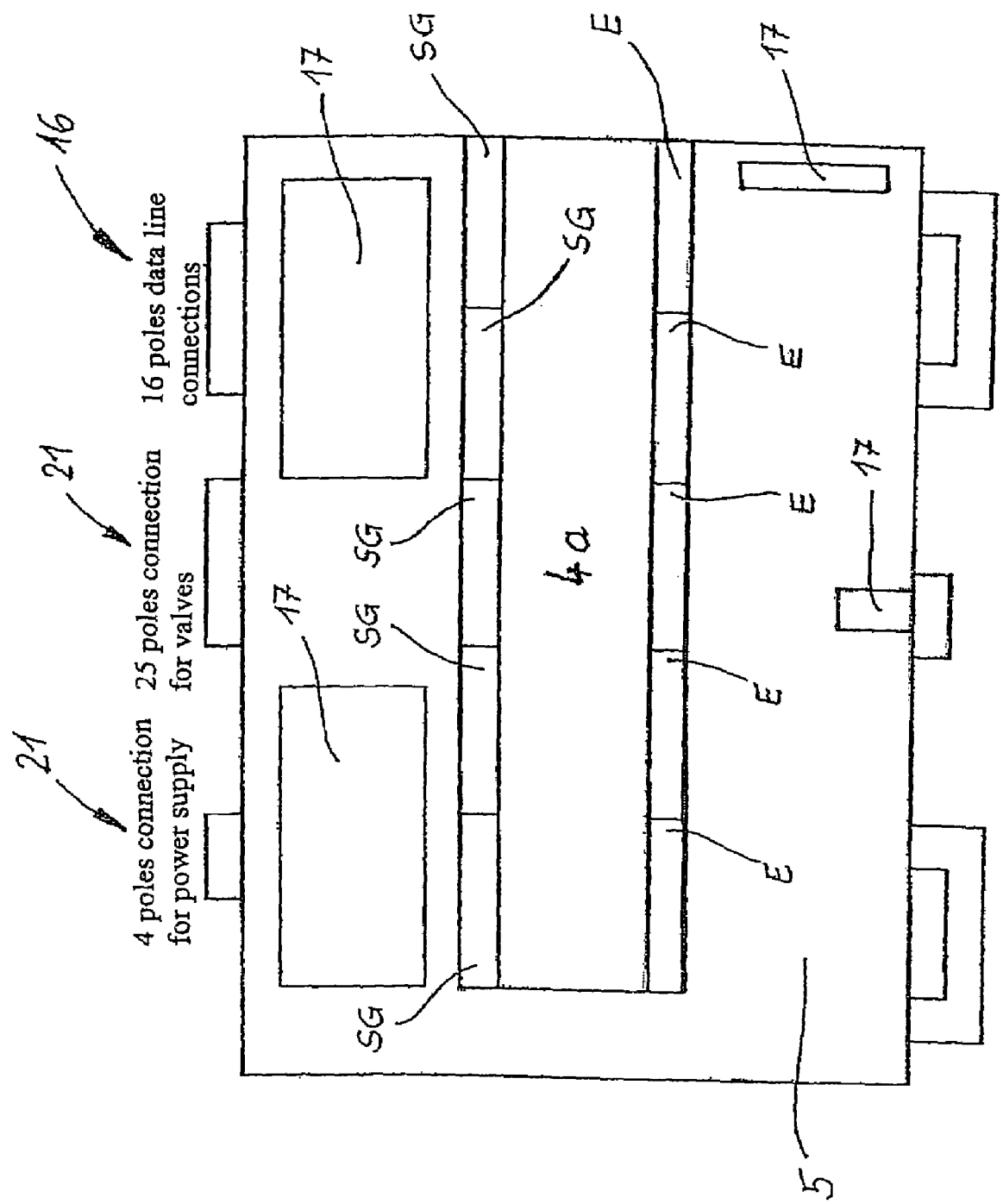

DETECTION DEVICE FOR IDENTIFYING OBJECTS IN A MATERIAL STREAM

CROSS REFERENCE TO RELATED APPLICATIONS

Applicants claim priority under 35 U.S.C. §119 of Austrian Application No. GM 450/2004 filed Jun. 29, 2004. Applicants also claim priority under 35 U.S.C. §365 of PCT/AT2005/000154 filed May 4, 2005. The international application under PCT article 21(2) was not published in English.

BACKGROUND OF THE INVENTION

The present invention relates to a detecting apparatus for detecting objects in a material flow, preferably consisting of cullet, with at least one optical transmitter unit consisting of several light sources being provided and at least one receiving unit which is associated with the transmitter unit and comprises a lens system, as well as an interposed detecting section which is flowed through by the material flow and to a sorting apparatus in which such a detecting apparatus is used.

DESCRIPTION OF THE PRIOR ART

Detecting apparatuses which detect foreign bodies by means of optical transmitter and receiver units in a material flow moved between the transmitter and receiver units, especially a stream of cullet, are known for example from AT 395.545 B. The transmitter units consist of light sources emitting light beams, preferably diode light sources, which are focused in the receiver unit via a lens system to a photoelectric cell. In the case of known detecting apparatuses the light sources are aligned parallel with respect to each other, as a result of which the emitted light beams also extend parallel with respect to each other in the direction of the receiver units. The aspect is problematic in this respect that the light beams extending parallel have different distances from the optical axis of the lens system of the receiver. It has long been known for a fact that optical projections by a lens are principally not free of errors and the aberration increases with the distance of the individual light beams from the optical axis.

The mentioned detecting apparatuses are also used in known sorting apparatuses. The material flow to be sorted, e.g. cullet, is moved past the transmitter and receiver units and the light beams are interrupted or allowed to pass through accordingly. The transmitter and receiver units are connected with a control unit which subsequently triggers blow-out nozzles situated downstream of the transmitter and receiver units. When a light beam of a transmitter unit is interrupted or the same is diminished beneath a certain threshold value, the control unit assumes that this interruption or diminishing was caused by a foreign body (i.e. no glass) and activates after a delay based on the distance of the blow-out nozzles from the light sources the blow-out nozzles which are directed towards the material flow and are associated with such transmitter and receiver units for which the interruption or diminishing of the light beam was registered, as a result of which the presumed foreign body is removed from the material flow, preferably to a waste container.

The above disadvantage in previously used detecting apparatuses leads to an imprecise blow-out process and to the fact that presumed foreign bodies are not detected exactly and remain in the material flow. Especially in the case of presumed foreign bodies which flow further away from the optical axis of a receiver unit in the material flow, the sharpness of focus is low and leads to erroneous interpretations concerning the material.

SUMMARY OF THE INVENTION

It is therefore the object of the present invention to avoid this disadvantage and to provide a detecting apparatus which substantially eliminates the error source in connection with the optical lens systems.

This is achieved by a detecting device in accordance with the invention.

This ensures that the light beams in the area of the point of intersection of the optical axis of the lens system impinge with the lens system and thus enable an optimal deflection of the light beams onto the photoelectric cell. Point of intersection shall in this case not mean a point per se in a mandatory fashion, but an area around the point of intersection which enables a deflection of the light beams onto the photoelectric cell arranged afterwards with a sufficient amount of security and precision. In practice, said area will be formed by a circle about the point of intersection with a diameter of approximately 2 mm. By eliminating the optical blur, a substantially improved blow-out performance of the blow-out nozzles of the sorting device can be achieved.

According to a preferred embodiment of the invention, the light sources of a transmitter unit are aligned in a plane in which the optical axis of the lens system of the associated receiver unit is also situated. In this case, the light sources in this plane merely need to be inclined about an angle relative to the optical axis in order to enable the light beams to impinge at the point of intersection of the optical axis with the lens system.

According to a further embodiment the plane extends perpendicular to the detecting section which is arranged as a transparent material chute. This means that transmitter unit and receiver unit with the lens system are situated precisely opposite each other.

In a further preferred embodiment of the invention the light sources of one transmitter unit are aligned in at least two planes extending parallel with respect to each other; preferably the planes extend parallel to the optical axis. Usually, the optical axis will extend between the two mentioned planes. The normal distance between the planes and the optical axis is either so low that it is merely necessary to have the aforementioned inclination of the alignment of the light sources in the respective pane about an angle to the projection of the optical axis into the plane in order to ensure sufficient deflection of the light beams to the point of intersection of the optical axis with the lens system.

If the distance between the planes and the optical axis too large in order to ensure a sufficiently precise deflection, then it is necessary in addition to the inclined alignment of the light source in the planes to align the plans, which means such that are converging in the direction of the point of intersection.

In certain preferred embodiments several transmitter units and receiver units plus lens system and photoelectric cell are arranged along the detecting section behind one another or also adjacent to one another (in order to cover the entire width of the detecting section). Each transmitter unit can consist of several light sources which may also be arranged in several parallel planes.

According to a further embodiment, the light source are preferably arranged directly beneath the transparent floor of the material chute, thus minimizing the likelihood of overlooking foreign bodies.

A new detecting apparatus in accordance with the invention may also be used in a known sorting apparatus with blow-out nozzles.

BRIEF DESCRIPTION OF THE DRAWINGS

A detailed description of the invention is provided below by reference to the enclosed drawings, wherein:

FIG. 4 shows a schematic view of a detecting apparatus.

DETAILED DESCRIPTION OF THE PREFERRED EMBODIMENTS

Figure 1:
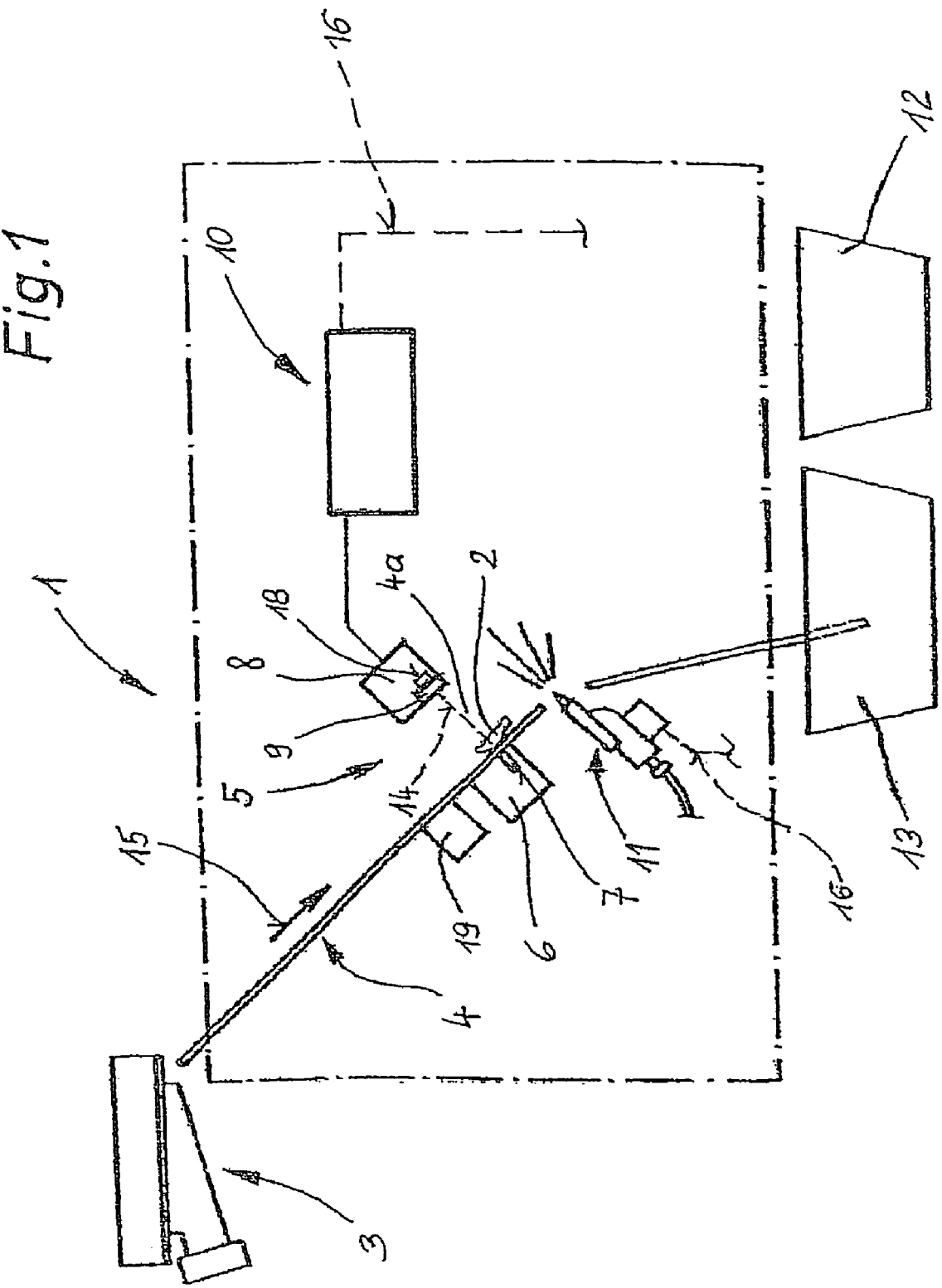
FIG. 1 shows a simplified schematic representation of the apparatus in accordance with the invention.

FIG. 1 schematically shows a sorting apparatus 1 for sorting out foreign bodies 2 such as pieces of metal, ceramic or earthenware for example from a flow of cullet material. In this apparatus 1, a material chute 4 is provided adjacent to the feeder station 3. In the lower section of said chute a detecting apparatus 5 is arranged for detecting foreign bodies 2 in the cullet flow. Said detecting apparatus 5 substantially consists of at least one transmitter unit 6 with successive pulsed light sources 7, preferably diode light sources, and at least one receiver unit 8 which comprises a lens system 9 and a photoelectric cell 18 arranged behind the same, and a control unit 10 which is connected with blow-out nozzles 11 which are arranged at the end of the material chute 4 and controls the same depending on the signals of the transmitter and receiver unit. The blow-out nozzles 11 which are arranged downstream of the transmitter and receiver unit 6, 8 at the end of the material chute 4 are simultaneously situated in a section in which the cullet material flow follows the curve of a bomb trajectory. When the blow-out nozzles 11 are activated by the control unit 10, the foreign bodies 2 are deflected from the cullet material stream, so that they fall into a waste container 12 and are thus separated from the cullet falling into another container 13.

The detecting apparatus 5 itself can be mounted as a so-called "black box" with very few manipulations on the sorting apparatus 1 and can also be removed again, so that an exchange can occur within a few minutes.

As already mentioned, the transmitter unit 6 comprises light sources 7, preferably diode light sources emitting straight light beams 14. FIG. 1 shows such a light beam 14 between the transmitter unit 6 and the receiver unit 8 in a simplified illustration. The light beam 14 is deflected by a lens system 9 which is a component of the receiver unit 8 to a photoelectric cell 18 (see FIG. 2). The signal thus produced is forwarded to the control unit 10.

The light sources 7 are arranged beneath the material chute 4 which is provided with an optically transparent configuration, and especially beneath the detecting section 4a, so that the cullet material stream will flow practically directly in front of the light sources 7. The alignment occurs in accordance with the invention in such a way that the light sources 7 are aligned with the lens system 9 towards the region of the point of intersection S of the optical axis of the lens system 9, irrespective of its arrangement and placement with respect to the receiver unit or the material chute 4.

Figure 2:
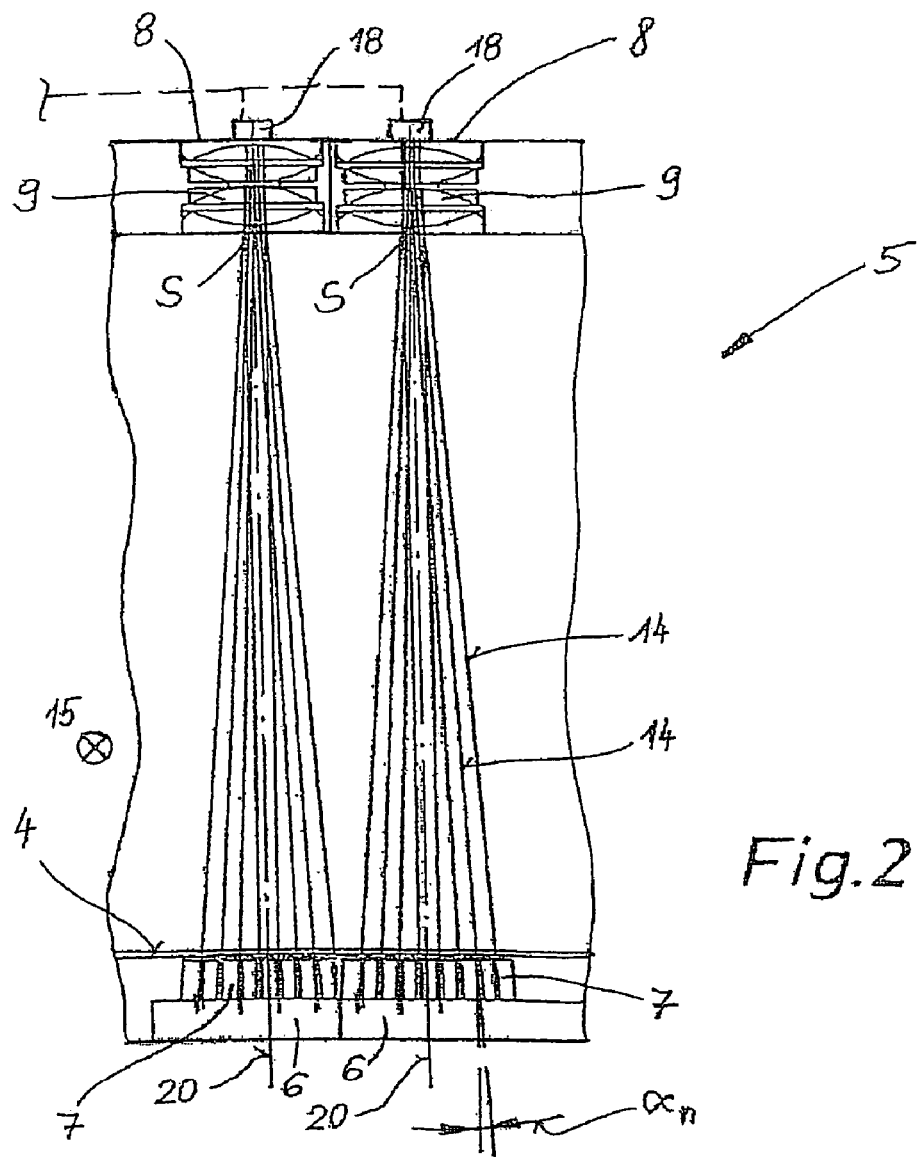
FIG. 2 shows a simplified schematic representation of the detecting apparatus.
Figure 3:
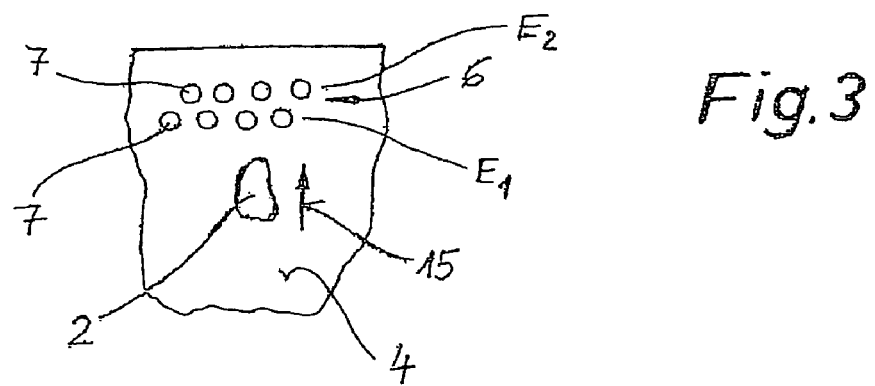
FIG. 3 shows a detailed view of the arrangement of the light sources of a transmitter device.

FIG. 2 and FIG. 3 show preferred embodiments of the light sources 7.

In FIG. 2, the light sources 7 of a transmitter unit 6 are arranged in a plane $E_1$, with the optical axis 20 of the lens system 9 of the respectively associated receiver unit 8 also being situated in said plane $E_1$. The direction of flow of the material shows perpendicular to the sheet in FIG. 2 and is labelled with reference numeral 15. FIG. 2 shows an embodiment with two transmitter units 6, each with a number of light sources 7 and two respectively associated receiver units 8 with a lens system 9 and a photoelectric cell 18 each. It is understood that the width of the material chute 4 can also be covered by one transmitter unit 6 and one receiver unit 8 or by more than two receiver and transmitter units 6, 8.

In accordance with the invention, a number of light sources 7, which are not those situated in the optical axis 20, are aligned in an inclined manner about an angle $(\alpha_{1,2,3,\ldots n})$ relative to the optical axis 20, so that the emitted light beams 14 impinge in a point of intersection S of the optical axis 20 of the respective lens system 9 of a receiver unit 8. It is ensured by such an alignment in accordance with the invention that the light beams 14 which impinge in an oblique manner are deflected parallel to the optical axis 20 and an optimal projection on the photoelectric cell 18 is achieved. Notice must be taken that in the case of this preferred embodiment of the invention the light beams 14 of the individual light sources 7 will never impinge simultaneously at the point of intersection S and interference can therefore never occur. The triggering of the light sources 7 occurs in a pulsed manner, so that one individual light source each of a transmitter unit 6 will be active at a given time. With the knowledge of the transmitter unit 6 which is active just now and the signal supplied by the photoelectric cell 18, the control unit 10 will decide whether the blow-out nozzle 11 associated with said transmitter/receiver unit 6, 8 should blow out or not in order to deflect the foreign body 2 to the mentioned waste container 12. The decision is based on the fact that a predetermined voltage threshold value obtained from the light intensity on the photoelectric cell 18 is fallen below or not.

FIG. 3 shows a schematic top view of a possible further preferred arrangement of light sources 7 behind the optically transparent material chute 4. As can be clearly seen, the light sources 7 are aligned in two planes $E_1, E_2$ behind one another and in a laterally offset manner in the direction of flow of the material, as a result of which an even more precise resolution of the detecting apparatus 5 is achieved. The planes $E_1, E_2$ of the light sources 7 can belong to either one transmitter unit 6 and thus also cooperate with a receiver unit 8 or each plane $E_1$, $E_2$ forms a transmitter unit 6 and therefore also cooperates with one associated receiver unit 8 each (i.e. in total with two receiver units 8).

The chosen embodiment depends substantially on whether the distance between the planes $E_1, E_2$ is sufficiently small in order to cooperate with a single lens system 9. In practice however, a single lens system 9 is necessary at a distance of approximately 8 to 10 mm. In this case the planes $E_1, E_2$ can even be aligned parallel with respect to each other. The optical axis 20 would then be located between the two planes $E_1, E_2$. The light beams 14 would still sufficiently impinge on the lens system 9 in the region of the point of intersection S, subject to an inclination about an about an angle $(\alpha_{1,2,3,\ldots n})$ in accordance with the invention for projection of the optical axis 20 into the planes $E_1, E_2$ that a perfect deflection to photoelectric cell 18 is possible.

Should the distance between the planes $E_1, E_2$ be larger so that a perfect deflection of the light beams 14 onto the photoelectric cell 18 is no longer possible, it is either necessary to use a further lens system 9 and thus a further photoelectric cell 18, as was already mentioned above, or the planes $E_1, E_2$ must be aligned accordingly so as to converge in the direction of the point of intersection S.

In a preferred embodiment, a detecting apparatus 5 (see FIG. 4) consists of five transmitter unit groups SG which work in parallel and each comprise thirty-two diode light sources 7. The diode light sources 7 of a transmitter unit group SG are combined on their part into four transmitter units 6 with eight each. Each transmitter unit group SG is associated with a receiver unit group E which consists of four receiver units 8. In accordance with the invention, the light beams emitted by each transmitter unit 6 are aligned towards the lens system 9 and subsequently to the photocell 18 of the receiver unit 8 associated with the respective transmitter unit 6. Each receiver unit group E thus comprises four receiver units 8 and thus four lens systems 9 and four photoelectric cells 18. Each receiver units 8 jointly comprise twenty lens systems 9 and twenty photoelectric cells 18. The detecting apparatus 5 shown in FIG. 4 further shows the connections 21 for power supply and for connection with the blow-out valves 11 and data line connections 16 and various operating elements 17.

All thirty-two diode light groups 7 of each of the transmitter unit groups SG working in parallel are activated successively within the cycle period of 1 ms in groups. The respectively first diode light sources of the transmitter units 6 of all transmitter unit groups SG are activated simultaneously. After their cut-off there is the activation of the respective second diode light sources 7 of the transmitter units 6 of all transmitter unit groups SG, etc. As a result, 160 signals (which corresponds to 32 lines) are detected in a cycle of the total of twenty photocells 18. This corresponds to the one-off detection of the entire sorting width of the material chute 4. Notice shall be taken at this point that the described embodiment shall merely be understood as an example and that the number of the transmitter unit groups SG and the diode light sources 7 and the receiver unit groups E, receiver units 8 and thus the lens systems 9 and the photoelectric cells 18 have been chosen at random and have proven to be reliable in practical tests. It is understood that it is completely clear to the person skilled in the art that other divisions can also lead to good results without moving out of the actual scope of protection of the invention.

The received analogue signals are subsequently converted by the control unit 10 into a voltage signal depending on the light quantity received by the photoelectric cells 18. Said received signals are each compared with a reference voltage and if the value falls below said reference voltage, a blow-out nozzle 11 associated with one of said photoelectric cells 18 is activated.

In order to increase the efficiency in the detection and removal of the foreign bodies 2 and to keep the removal of useful material as low as possible, an additional non-ferrous metal detector 19 is provided in the region of the material chute 4 upstream of the described transmitter and receiver units 6, 8. Said non-ferrous metal detector 19 is also connected with the control unit 10. Its supplied data are linked with those of the transmitter and receiver units 6, 8 and contribute towards an additional improvement in the digital preparation of an image of the cullet material flow.

It finally needs to be mentioned that the subject matter of the invention is the alignment of the light sources 7, preferably diode light sources, of a transmitter unit 6 relative to the optical axis 20 of the lens system 9 of the associated receiver unit 8, with detecting apparatuses and sorting apparatuses according to the preamble of claim 1. As long as this concerns detecting apparatuses or sorting apparatuses of this kind, any change in the manner of signal processing or the decision-making process as to when a blow-out nozzle 11 is activated, the handling of the threshold values, etc. shall not lead out of the scope of the invention because the same shall be understood only in an exemplary manner on the basis of the described embodiment, but in no way as limiting.

The invention claimed is:

1. A detecting apparatus for detecting objects in a material flow comprising:
    (a) at least one optical transmitter unit comprising a plurality of light sources radiating light in a straight line;
    (b) at least one receiver unit comprising a photocell and at least one lens system having an optical axis, said at least one receiver unit being associated with the at least one transmitter unit; and
    (c) an interposed detecting section, the material flow flowing through the detecting section;
    wherein the light sources of the at least one optical transmitter unit are aligned to the region of the point of intersection of the optical axis of the at least one lens system with the at least one lens system.

2. The detecting apparatus according to claim 1, wherein the plurality of light sources are arranged in a plane jointly with the optical axis, said plurality of light sources including light sources outside of the optical axis and aligned at an angle relative to the optical axis.

3. The detecting apparatus according to claim 2 wherein the detecting section is arranged as an optically transparent material chute having a floor, and wherein the plane extends perpendicular to the floor of the material chute.

4. The detecting apparatus according to claim 1, wherein the light sources are aligned along several planes extending parallel with respect to each other.

5. The detecting apparatus according to claim 4, wherein the planes extending parallel with respect to each other extend parallel to the optical axis.

6. The detecting apparatus according to claim 1, wherein the light sources are aligned along planes which converge with respect to each other in the point of intersection.

7. The detecting apparatus according to claim 1, wherein several optical transmitter units and receiver units are arranged behind one another in a direction of the material flow.

8. The detecting apparatus according to claim 1 wherein several optical transmitter units and receiver units are arranged next to one another over an entire width of the detecting section.

9. The detecting apparatus according to claim 3, wherein the light sources are arranged beneath the floor of the material chute.

10. A sorting apparatus for recognizing objects in a material flow comprising:
    (a) a detecting apparatus;
    (b) a control unit connected with the detecting apparatus; and
    (c) a plurality of blow-out nozzles arranged downstream of the detecting apparatus;
    wherein the control unit controls the blow-out nozzles to deflect foreign bodies from the material flow to a defined location; and
    wherein the detecting apparatus comprises at least one optical transmitter unit comprising a plurality of light sources radiating light in a straight line, at least one receiver unit comprising a photocell and at least one lens system having an optical axis, said at least one receiver unit being associated with the at least one transmitter unit, and an interposed detecting section, the material flow flowing through the detecting section, wherein the light sources of the at least one optical transmitter unit are aligned to the region of the point of intersection of the optical axis of the at least one lens system with the at least one lens system.

* * * * *

UNITED STATES PATENT AND TRADEMARK OFFICE
CERTIFICATE OF CORRECTION

PATENT NO. : 7,639,352 B2  Page 1 of 1
APPLICATION NO. : 11/629970
DATED : December 29, 2009
INVENTOR(S) : Huber et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 406 days.

Signed and Sealed this

Ninth Day of November, 2010

David J. Kappos
*Director of the United States Patent and Trademark Office*